US00PP27421P3

(12) United States Plant Patent
Leis et al.

(10) Patent No.: US PP27,421 P3
(45) Date of Patent: Nov. 29, 2016

(54) APPLE TREE NAMED 'FUCIV51'

(50) Latin Name: *Malus domestica* Borkh
Varietal Denomination: FUCIV51

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara FE (IT); Alessio Martinelli, Ferrara (IT)

(73) Assignee: C.I.V.—Consorzio Italiano Vivaisti-Società Consortile A R.L., Comacchio (IT)

( * ) Notice: Subject to any disclaimer, the term of this patent is extended or adjusted under 35 U.S.C. 154(b) by 191 days.

(21) Appl. No.: 14/121,688

(22) Filed: Oct. 8, 2014

(65) Prior Publication Data

US 2015/0101087 P1 Apr. 9, 2015

(30) Foreign Application Priority Data

Oct. 9, 2013 (EM) ..... 2013/2586

(51) Int. Cl.
*A01H 5/00* (2006.01)
*A01H 5/08* (2006.01)

(52) U.S. Cl.
USPC ..... Plt./168
CPC ..... *A01H 5/0875* (2013.01)

(58) Field of Classification Search
USPC ..... Plt./168
CPC ..... A01H 5/0875
See application file for complete search history.

*Primary Examiner* — Kent L Bell
(74) *Attorney, Agent, or Firm* — Foley & Lardner LLP

(57) ABSTRACT

A new and distinct *Malus domestica* Borkh. apple tree variety named 'FUCIV-51' is a naturally occurring mutation of the Fuji 'NAGAFU-12' apple, particularly characterized by a very large area of over color, in particular in warm areas with low day-night thermic excursion; red coloration on most part of the unexposed side of the fruit; and intense purple-red over color.

4 Drawing Sheets

Figure 1:
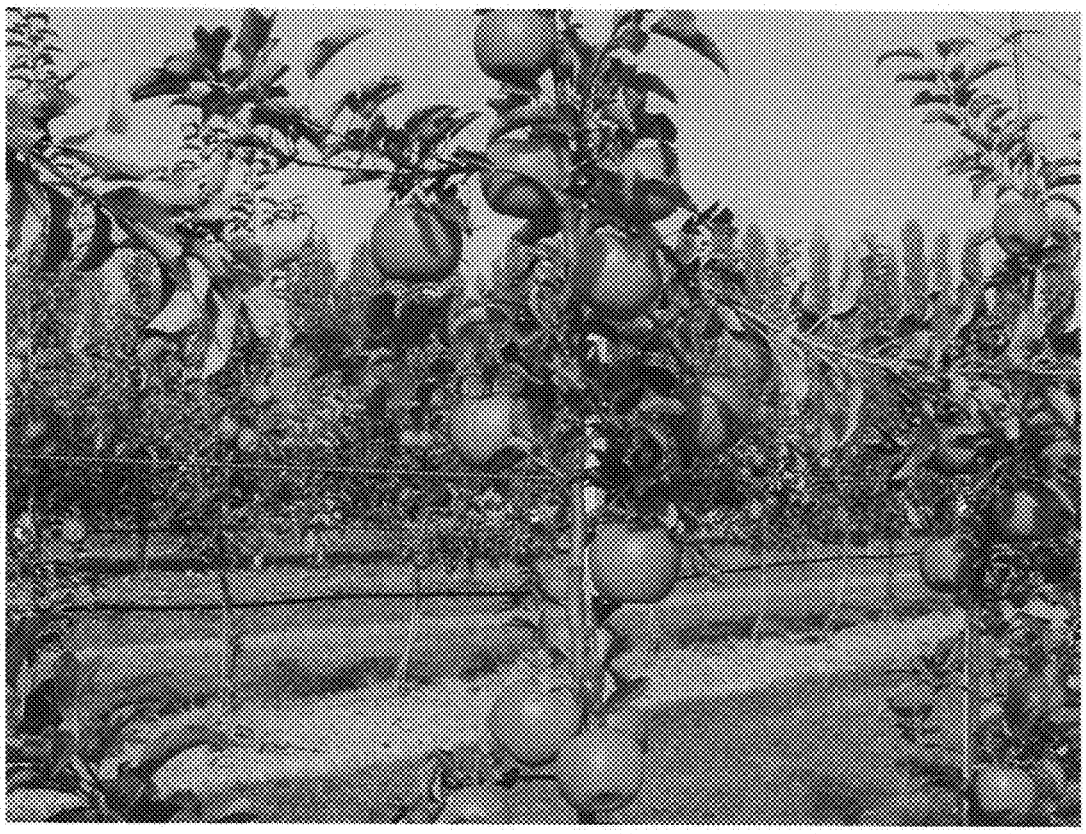

Latin name of the genus and species of the plant claimed: *Malus domestica* Borkh.

Variety denomination: 'FUCIV51'.

PRIORITY CLAIM

This application claims priority under 35 U.S.C. §119(f) to European Community Plant Variety Office Application No. 2013/2586 filed Oct. 9, 2013.

BACKGROUND OF THE INVENTION

The present invention relates to a new and distinct variety of apple tree, botanically known as *Malus domestica* of the Rosaceae family, and hereinafter referred to by the variety denomination 'FUCIV51 '.

The new *Malus* 'FUCIV51' was discovered by the inventors, Michelangelo Leis and Alessio Martinelli, in the summer 2005 as a naturally occurring mutation branch in a block of Fuji apple trees designated as 'NAGAFU-12'(unpatented), growing in a cultivated area of an orchard in Ferrara, Italy. The tree of the new variety was showing fruits distinctly different in appearance, more intense and diffused red skin surface color, from the fruit of the adjacent Fuji 'NAGAFU-12' trees.

Asexual reproduction of the new *Malus* 'FUCIV51' trees started by grafting onto M9 rootstock in February 2009 in a new testing field in S. Giuseppe di Comacchio (Ferrara), Italy. Some trees of Fuji 'NAGAFU-12' (unpatented), and Fuji 'Aztec' were grafted on M9 rootstocks in the same row and at the same time as 'FUCIV51' was first grafted on M9 rootstocks. First fruiting of the 'FUCIV51' trees occurred in 2007, and revealed that fruit produced from the 'FUCIV51' trees possessed characteristics which clearly distinguished 'FUCIV51' from other Fuji apple varieties known to the Inventors. Asexual reproduction of 'FUCIV51' has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'FUCIV51' which in combination distinguish this apple tree as a new and distinct variety from the other Fuji strains:

1. Very large area of over color, in particular in warm areas with low day-night thermic excursion;
2. Red coloration on most part of the unexposed side of the fruit and
3. Intense purple red over color.

In comparison to the parental variety Fuji 'NAGAFU-12', 'FUCIV51' produces fruit with a more intense and diffused red skin surface color. The two varieties differ primarily in the traits listed in Table 1.

TABLE 1

| Characteristic in which the origin variety is different | State of expression of origin variety 'NAGAFU-12' | State of expression of candidate variety 'FUCIV51' |
|---|---|---|
| Fruit: relative area of over color | Small | Very Large |
| Fruit: hue of over color | Brick red | Purple red |

TABLE 1-continued

| Characteristic in which the origin variety is different | State of expression of origin variety 'NAGAFU-12' | State of expression of candidate variety 'FUCIV51' |
|---|---|---|
| Fruit: pattern of over color | Weakly solid flush with some defined stripes. | Only solid flush |

Of the many commercial varieties known to the present inventors, the most similar in comparison to 'FUCIV51' is the variety 'Raku Raku' (unpatented), in the following characteristics described in Table 2:

TABLE 2

| Characteristic in which the similar variety is different | State of expression of similar variety 'RAKU RAKU' | State of expression of candidate variety 'FUCIV51' |
|---|---|---|
| Fruit: relative area of over color | Medium | Very Large |
| Fruit: hue of over color | Red | Purple red |
| Fruit: pattern of over color | Weakly solid flush with defined stripes. | Only solid flush |

BRIEF DESCRIPTION OF THE PHOTOGRAPHS

The accompanying photographs illustrate the overall appearance of the new apple tree 'FUCIV51' showing the colors as true as is reasonably possible with color reproductions of this type. Color in the photographs may differ slightly from the color value cited in the detailed botanical description, which accurately describe the color of 'FUCIV51'.

Figure 2:
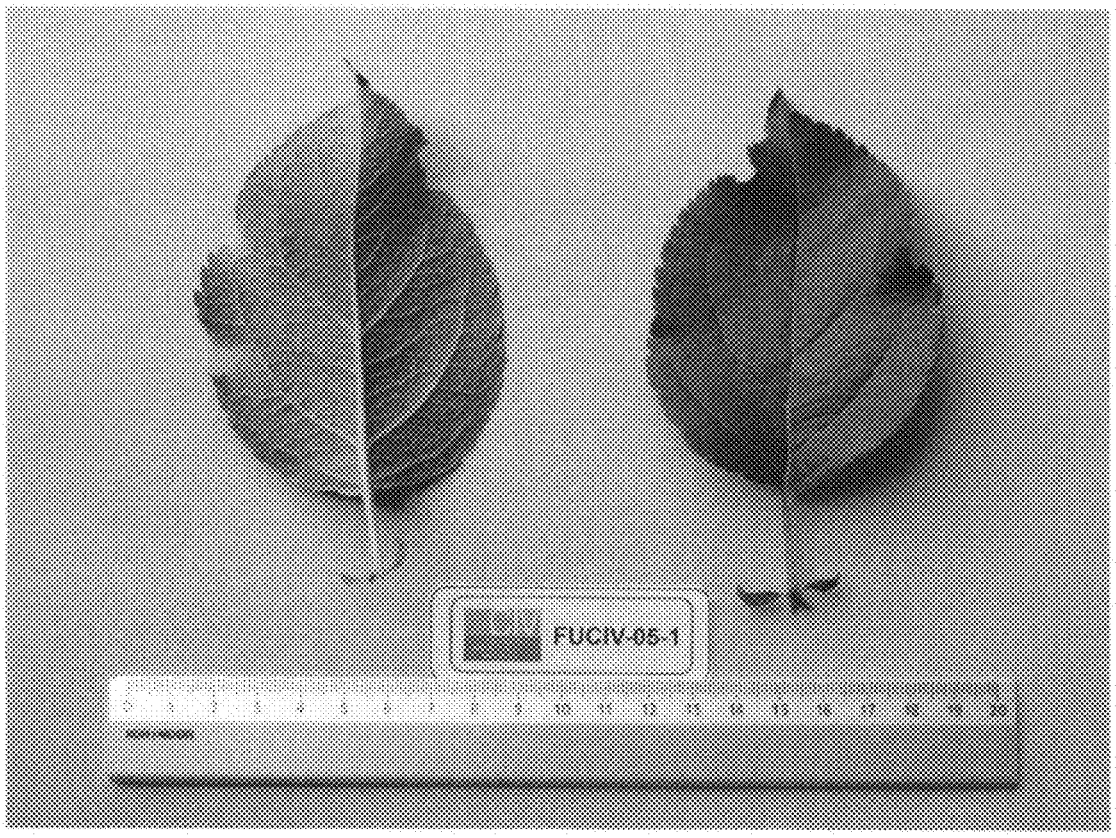
Figure 3:
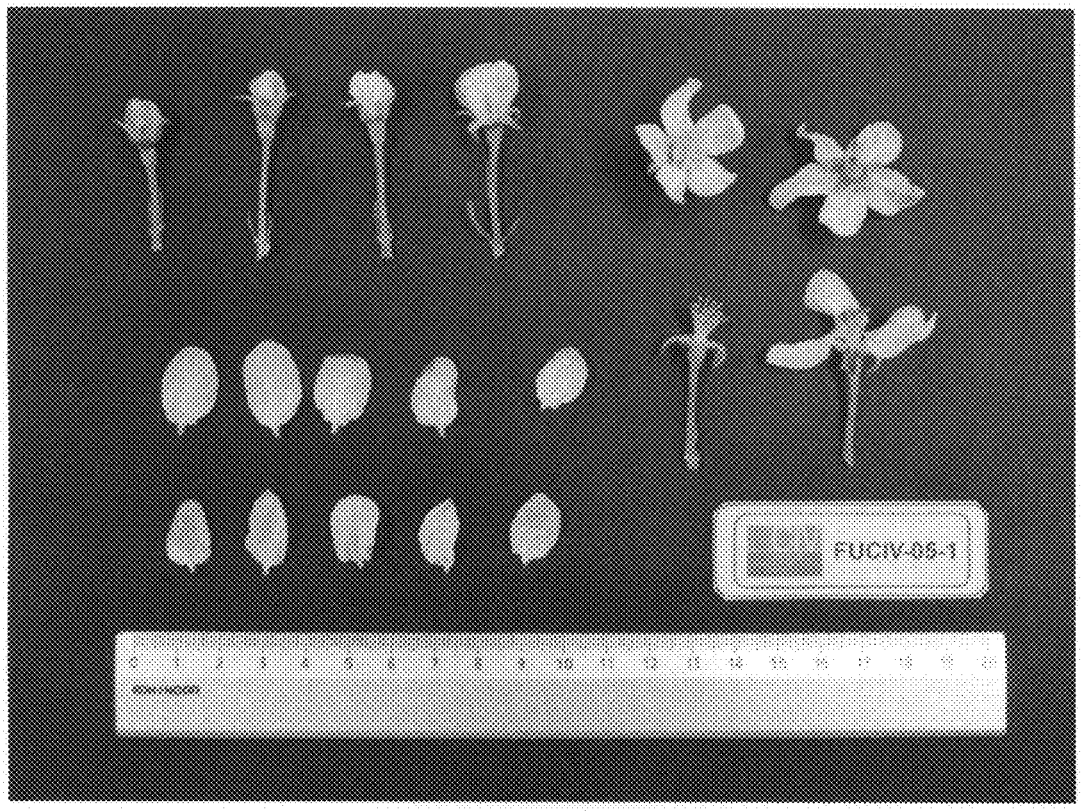
Figure 4:
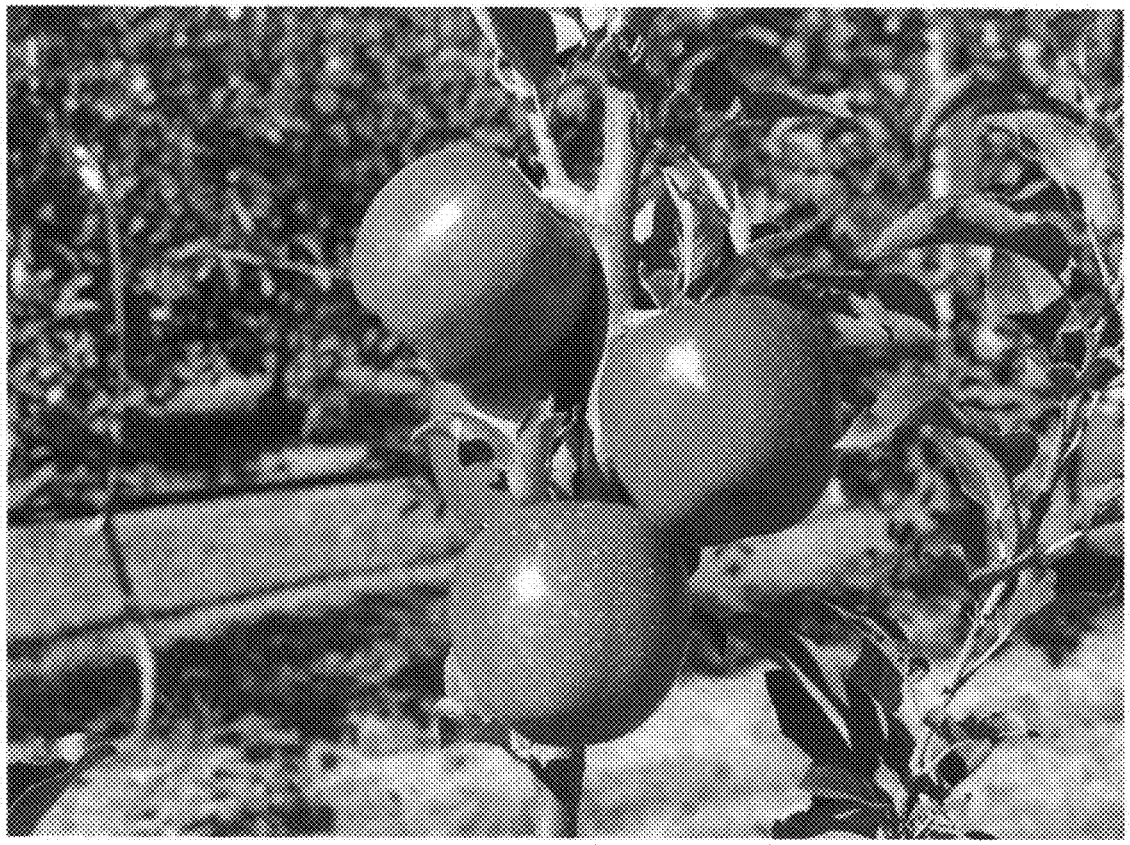

FIG. 1: illustrates a typical tree of 'FUCIV51';
FIG. 2: illustrates typical leaves of 'FUCIV51';
FIG. 3: illustrates typical flowers of 'FUCIV51'; and
FIG. 4: illustrates typical fruit of 'FUCIV51'.

DETAILED BOTANICAL DESCRIPTION

'FUCIV51' has not been observed under all possible environmental conditions. The phenotype of the new variety may vary with variations in environment such as temperature, light intensity, and day length without any change in the genotype of the plant.

The aforementioned photographs, together with the following observations, measurements and values describe trees of 'FUCIV51' as grown in the apple farm in S. Giuseppe di Comacchio, Ferrara, Italy, under conditions which closely approximate those generally used in commercial practice. The apple farm where 'FUCIV51' is grown is situated near the Adriatic sea (44°45' North, 12° 11' East) and is zero (0) meters above sea level. The soil of the apple farm where 'FUCIV51' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'FUCIV51' trees that were grown in the apple farm in S. Giuseppe di Comacchio, Ferrara, Italy, from 2009 to 2012. All trees were of cropping maturity. Quantified measurements are expressed as an average of measurements taken from a number of individual trees of 'FUCIV51'. The measurements of any individual tree, or any group of trees, of the new variety may vary from the stated average.

Color references are made to The Royal Horticultural Society (London) Colour Chart (R.H.S.), except where general colors of ordinary significance are used. Color values were taken under daylight conditions at approximately at 10:00 am in S. Giuseppe di Comacchio, Ferrara, Italy.

All of the trees of 'FUCIV51', insofar as they have been observed, have been identical in all the characteristics described below.

Classification:
- *Botanical.*—Malus domestica.

Parentage: Naturally occurring mutation (sport) from Fuji 'NAGAFU-12'.

Propagation: Budding and grafting on M9 rootstock.

Growing conditions:
- *Light intensities.*—Full sunlight.
- *Temperature.*—During day, grown in range of 0° C. to 35° C., and during night, grow in range of −5° C. to 25° C.
- *Fertilization.*—Manure every year.
- *Growth regulators.*—Not used.
- *Pruning or trimming requirements.*—The trees observed are grown to Spindle, regular pruning is essential to maximize light penetration and maintain the tree shape.

Tree:
- *Age.*—Observed trees were four (4) years old.
- *Vigor.*—Vigorous, same as Fuji 'NAGAFU-12'.
- *Form.*—Upright and conical with narrow branch angles.
- *Habit.*—A medium sized tree with one trunk and one (1) leader; main branches spreading; crown symmetrical and regular in shape.
- *Branching habit.*—Main branches angle is 40° to 60° with respect to trunk if allowed to grow naturally.
- *Density.*—Medium density.
- *Cropping behavior.*—Early beginning of production; very high productivity. Occasionally biennial bearing.
- *Type of bearing.*—Typically long shoot, presence of spur on 2-3 year old shoots.
- *Production (four year).*—About 15 Kg.
- *Size at maturity.*—Height: About 3.1 m. Spread: About 1.40 m.
- *Trunk.*—Height (up to leaders): About 2.7 m. Diameter: About 48 mm as measured 20 cm above point of grafting. Texture: At first, smooth with numerous lenticels, then shallow furrows and scaly ridges.
- *Bark color.*—Primarily Greyed green, RHS 197C, with greyed orange RHS 164 C, underbark.
- *Trunk lenticels.*—Length: About 2.0 mm. Width: About 0.9 mm. Color: Greyed orange, RHS 164 C. Density: About 5 to 6 per $cm^2$.
- *Branches.*—Number per tree: About 17-20. Length: Varies due to pyramidal shape of tree; at three (3) year, maximum of 85 cm to 100 cm; minimum about 35 cm. Diameter (at 3 year old): About 9.5 mm to 16 mm. Surface texture: Smooth. Pubescence: Pubescence on new wood, becoming glabrous on older wood. Color: Mature (after about three (3) year old): Greyed brown, RHS 199 B. New Growth: Greyed orange, RHS 165 A. Internode length: About 2.5 cm to 4.5 cm. Internode diameter: About 11.0 mm to 15.0 mm. Branch lenticels: Length: About 1.5 mm. Width: About 0.52 mm. Color: Greyed yellow, RHS 161 A. Density: About 7 to 9 per $cm^2$.

*Spur.*—Present: Yes. Distance between each spur: On the three year old branches, the distance is about 30.0 mm to 55.0 mm. Diameter of each spur: About 6.0 mm. Number of fruit per spur: About 3 to 5 without thinning.

Foliage:

*Arrangement.*—Alternate, simple, petiolated.

*Lamina.*—Size: Length: About 91 mm (from $3^{rd}$ to $5^{th}$ fully expanded leaf). Width: About 59 mm (from $3^{rd}$ to $5^{th}$ fully expanded leaf). Length/width ratio: 1.55. Overall Shape: Broad-elliptical. Base shape: Broad. Apex shape: Acuminate. Margin: Serrate. Texture: Upper surface: Smooth and glossy. Under surface: Weak pubescence on entire surface. Attitude in relation to shoot: Outwards. Color (mature leaves): Upper surface: Green, RHS 137 A. Under surface: Yellow green, RHS 148 B. Color (immature leaves): Upper surface: Green, RHS 138 B. Under surface: Green, RHS 138 C.

*Venation.*—Type: Prominent pinnate venation from central vein to the leaf edge. Color: Green, RHS 139 D.

*Petiole.*—Length: About 26.3 mm. Diameter: About 1.7 mm. Texture: Finely pubescent. Color: Yellow green RHS 147 D with anthocyanins red purple coloration on base RHS 60 A.

*Stipule.*—Arrangement: adnate, in pairs, thin and pointed. Distance of stipules from basal attachment of petiole: About 1.0 mm to 2.5 mm. Length: About 5.0 mm to 12.5 mm. Width: About 0.63 mm to 2.89 mm.

Inflorescence:

*Blooming time.*—Full bloom based on average of eight (8) years of observation, from 2007 to 2014, April $12^{ft}$ in San Giuseppe di Comacchio (Ferrara) Italy.

*Blooming period.*—About 8 to 12 days.

*Fragrance.*—Slight.

*Type.*—Inflorescence.

*Number of flowers per inflorescence.*—About 5 to 6.

*Inflorescence size.*—Diameter: About 60 mm. Depth: About 45 mm.

*Buds.*—Terminal Buds: Number per spur: Typically one per spur. Shape: Pointed. Length: About 7.5. Width: About 4.0. Texture: Slightly pubescent. Color: Apex, brown RHS 200 A, and base, brown RHS 200 B.

*Petals.*—Arrangement: Intermediate. Number per flower: Five. Size: Length: Average about 18.0 mm. Width: Average about 11.3 mm. Length/width ratio: 1.59. Overall shape: Elliptic elongated. Apex shape: Obtuse. Base shape: Broad. Texture (upper surface): Smooth. Texture (lower surface): Smooth. Margin: Entire. Color (upper surface): White, RHS 155 D. Color (lower surface): White, RHS 155 D with shade red-purple RHS 73 B.

*Sepals.*—Number per flower: Five. Size: Length: About 7.0 mm. Width: About 3.5 mm. Length/width ratio: 2.0. Overall shape: Lanceolate, recurved downward. Apex shape: Acute. Texture (upper surface): Hairy. Texture (lower surface): Hairy. Margin: Entire. Color (upper surface): Green, RHS 138 B. Color (lower surface): Green, RHS 139 D.

*Pedicel.*—Length: 20 to 30 mm. Diameter: in the middle 1.5 mm to 2 mm. Texture: Tomentose. Color: Green, RHS 139 D.

Fruit:

*Keeping quality.*—Excellent, quality is similar to that of standard Fuji. It has a long shelf life up to two weeks without losing firmness and juiciness.

*Maturity when described.*—Ripen for eating, late harvest period; first week of October in S.Giuseppe di Comacchio (Ferrara) Italy.

*Maturity period after full bloom.*—About 177 days after full bloom on April $13^{th}$.

*Date of first and last picking (harvest).*—About October $7^{th}$ and last picking October $12^{ft}$ in S.Giuseppe di Comacchio (Ferrara) Italy (North 44°45'46.2", East 012°11'31.9") in year 2013).

*Type.*—Pome.

*General shape.*—Round to slight flat.

*Average weight.*—About 312 g.

*Fruit size.*—Average height: About 78.9 mm. Average diameter (at widest point): About 88.4 mm. Position of maximum diameter: in the middle. Height/thickness ratio: 0.89.

*Stem.*—Length: About 25 mm. Diameter: About 2.4 mm. Color: Yellow green RHS 146 D.

*Stalk cavity.*—Depth: About 18 mm. Width: About 44 mm.

*Eye basin.*—Depth: About 14 mm. Width: About 38 mm. Crowning at calyx end: Absent or very weak. Position of sepals: Erect. Calyx tube: Partly open.

*Skin.*—Thickness: About 0.3 mm. Texture: Glossy. Bloom: medium to low. Greasiness: Absent. Firmness (at picking time): 7 to 8 $kg/cm^2$. Overcolor Color: Purple red, RHS 60 A. Percentage of skin surface with overcolor color: Very large. Pattern of overcolor: Only solid flush. Intensity of overcolor: Very bright. Ground color: Greyed yellow RHS 160 A. Skin Lenticels: Length: About 1.1 mm. Width: About 0.92 mm. Color: Greyed orange RHS 164 B. Density: About 3 per $cm^2$ in the central area of the surface.

*Flesh.*—Color: Yellow, RHS 2 D. Texture: Firm, crispy and juicy. Aroma: Medium. Eating quality: Good, with high level of sugar and good acidity. Sugar content (at picking time): 14.5 to 16 Brix. Acidity/Starch (at picking time): Acidity 5 to 6 g/lt Malic acid. Starch four (4) Laimburg scale 1 to 4. Core: Symmetry of core: Slightly asymmetric. Distinctness of core lines: Medium. Locules: Number (per fruit): Five (5). Length: About 11.8 mm. Width: About 4.2 mm. Form: Closed or partly open.

Seeds:

*Number per fruit.*—About 6 to 9.

*Number per locule.*—One (1) or Two (2).

*Shape.*—Elliptic.

*Length.*—About 8.7 mm.

*Width.*—About 5.2 mm.

*Texture.*—Smooth.

*Color.*—Greyed orange RHS 165 A.

Reproductive organs:

*Androecium.*—Stamen: Number per flower: About 18 to 20. Length: About 9.0 mm. Anther: Shape: Ovoid. Length: About 2.7 mm. Color: Yellow, RHS 9 C.

Filaments: Length: About 7.2 mm. Color: Green white, RHS 157 C. Pollen: Amount: Abundant. Color: Yellow orange, RHS 15 C. Pollination Requirements: It is important to use compatible pollinating varieties such as crab apple '*Malus* Evereste'.

*Gynoecium.*—Pistils: Quantity: Five (5). Length: About 10.0 mm. Style: Length: About 9.5 mm. Width: About 0.25 mm. Color: Yellow green, RHS 145 C. Stigmas: Shape: Funnel shape with receptive surface on top. Length: About 1.0 mm. Width: About 0.5 mm. Color: Yellow, RHS 145 B. Ovary: Length: About 3.7 mm. Width: About 2.6 mm. Color: Yellow green, RHS 144 A.

Use: Fresh market.

Disease/pest resistance: Similar to standard Fuji no resistance or susceptibility observed as of this time.

Disease/pest susceptibility: For both the tree and fruit, identical to the standard Fuji apple trees and other commonly used Fuji varieties known to the inventor.

Winter hardiness: Tolerant to temperatures down to −10° C. without observed damage to wood and buds of dormant Apple trees; but open flowers and young fruitlets are killed by exposure to −3° C., depending on the length of exposure.

Drought/heat tolerance: Tolerant to temperatures up to 35° C., growth is limited by drought periods without irrigation.

Shipping/storage characteristics: Good storability, identical to the standard Fuji apple.

We claim:

1. A new and distinct variety of *Malus domestica* apple tree named 'FUCIV-51', as illustrated and described herein.

* * * * *